United States Patent
Weisman et al.

(10) Patent No.: US 9,918,860 B2
(45) Date of Patent: Mar. 20, 2018

(54) RAPID EXCHANGE STENT DELIVERY SYSTEM

(71) Applicant: Boston Scientific Scimed, Inc., Maple Grove, MN (US)

(72) Inventors: Michal Weisman, Fair Lawn, NJ (US); Jacob Graham, Olmsted Township, OH (US); Gary J. Leanna, Holden, MA (US); John A. Griego, Blackstone, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/992,258

(22) Filed: Jan. 11, 2016

(65) Prior Publication Data

US 2016/0120675 A1    May 5, 2016

Related U.S. Application Data

(63) Continuation of application No. 13/300,111, filed on Nov. 18, 2011, now Pat. No. 9,265,637.

(60) Provisional application No. 61/415,660, filed on Nov. 19, 2010.

(51) Int. Cl.
| | |
|---|---|
| *A61F 2/95* | (2013.01) |
| *A61F 2/04* | (2013.01) |
| *A61M 25/01* | (2006.01) |
| *A61M 27/00* | (2006.01) |

(52) U.S. Cl.
CPC .......... *A61F 2/95* (2013.01); *A61F 2002/041* (2013.01); *A61F 2002/9511* (2013.01); *A61F 2220/0016* (2013.01); *A61M 25/01* (2013.01); *A61M 27/008* (2013.01); *A61M 2025/0183* (2013.01)

(58) Field of Classification Search
CPC .............. A61F 2002/9511; A61F 2/95; A61M 2025/0183
See application file for complete search history.

(56) References Cited

U.S. PATENT DOCUMENTS

| | | | |
|---|---|---|---|
| 5,238,004 A | 8/1993 | Sahatjian et al. | |
| 5,372,600 A * | 12/1994 | Beyar | A61F 2/95 606/194 |
| 6,508,803 B1 | 1/2003 | Horikawa et al. | |

(Continued)

FOREIGN PATENT DOCUMENTS

| | | |
|---|---|---|
| EP | 2640325 B1 | 7/2016 |
| JP | 2000152985 A | 6/2000 |

(Continued)

*Primary Examiner* — Julie A Szpira

(57) ABSTRACT

Stent delivery systems and methods for making and using stent delivery systems are disclosed. An example stent delivery system may include a guide member having a proximal portion and a distal portion. A stent may be disposed about the distal portion of the guide member. The stent may have a wall having an opening formed therein. A pusher member may be disposed about the guide member and positioned proximal of the stent. A holding filament may be disposed at the opening and may extend to the proximal portion of the guide member. The holding filament may be configured to releasably secure the position of the stent relative to the pusher member. The holding filament may be releasable from the stent independently of movement of the guide member.

20 Claims, 19 Drawing Sheets

(56) References Cited

U.S. PATENT DOCUMENTS

| | | | | |
|---|---|---|---|---|
| 6,576,005 | B1* | 6/2003 | Geitz | A61F 2/95 600/101 |
| 6,764,484 | B2* | 7/2004 | Richardson | A61M 25/0023 604/523 |
| 9,265,637 | B2 | 2/2016 | Weisman et al. | |
| 2005/0177043 | A1* | 8/2005 | Windheuser | A61M 25/0097 600/434 |
| 2007/0293929 | A1* | 12/2007 | Aoba | A61F 2/95 623/1.11 |
| 2009/0143849 | A1* | 6/2009 | Ozawa | A61F 2/94 623/1.11 |
| 2009/0312829 | A1* | 12/2009 | Aoba | A61F 2/94 623/1.11 |

FOREIGN PATENT DOCUMENTS

| | | |
|---|---|---|
| WO | 2008034106 A2 | 3/2008 |
| WO | 2012068508 A1 | 5/2012 |

\* cited by examiner

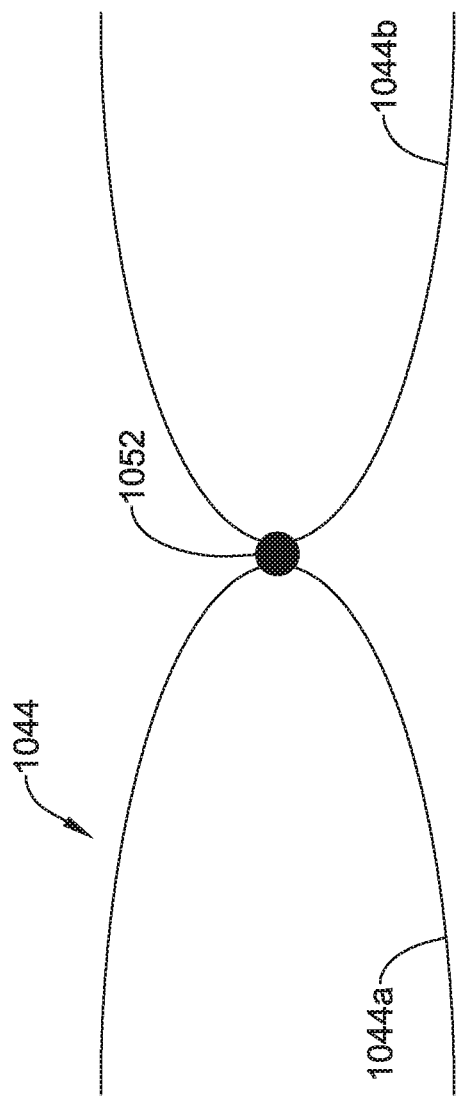

RAPID EXCHANGE STENT DELIVERY SYSTEM

CROSS REFERENCE TO RELATED APPLICATIONS

This application is a Continuation of U.S. application Ser. No. 13/300,111, filed Nov. 18, 2011, which claims the benefit of U.S. Provisional Application No. 61/415,660, filed Nov. 19, 2010, the entire disclosure of which is incorporated herein by reference.

FIELD OF THE INVENTION

The present invention pertains to medical devices and methods for manufacturing medical devices. More particularly, the present invention pertains to medical devices for delivering stents to the biliary tract and/or the pancreatic tract.

BACKGROUND

A wide variety of intraluminal medical devices have been developed for medical use, for example, use in the biliary tract. Some of these devices include guidewires, catheters, stents, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices or components thereof. An example medical device may be a stent delivery system that includes a guide member having a proximal portion and a distal portion. A stent may be disposed about the distal portion of the guide member. The stent may have a wall having an opening formed therein. A pusher member may be disposed about the guide member and positioned proximal of the stent. A holding filament may be disposed at the opening and may extend to the proximal portion of the guide member. The holding filament may be configured to releasably secure the position of the stent relative to the pusher member. In addition, the holding filament may be releasable from the stent independently of movement of the guide member.

An example method for delivering a biliary or pancreatic stent may include providing a stent delivery system. The stent delivery system may include a guide member having a proximal portion and a distal portion. A stent may be disposed about the distal portion of the guide member. The stent may have a wall having an opening formed therein. A pusher member may be disposed about the guide member and positioned proximal of the stent. A filament may be disposed at the opening and may extend to the proximal portion of the guide member. The filament may be configured to releasably secure the position of the stent relative to the pusher member. In addition, the filament may be releasable from the stent independently of movement of the guide member. The method may also include advancing the stent delivery system along a body lumen to a position adjacent to an area of interest and releasing the filament from the stent.

An example delivery system for delivering a biliary or pancreatic stent may include a guide tube. A drainage stent may be disposed about the guide tube. The drainage stent may be tubular and may have a tube wall with an opening formed therein. A push catheter may be disposed about a portion of the guide member proximal of the drainage stent. The delivery system may also include filament for securing the position of the drainage stent relative to the push catheter. The stent may be configured to be in either a first configuration where the stent is releasably secured relative to the push catheter with the filament or a second configuration where the filament is released from the stent. The guide tube may extend through the stent in both the first and second configurations.

The above summary of some embodiments is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 19 is a plan view of another example arrangement for a holding filament.

Figure 1:
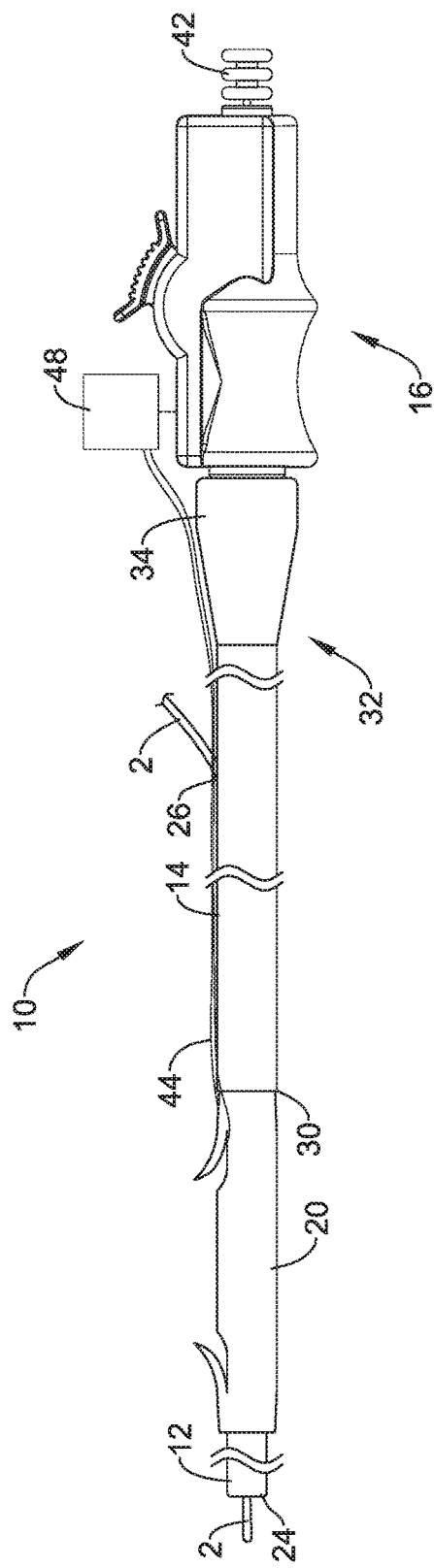
FIG. 1 is a plan view of an example stent delivery system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

A wide variety of biliary, endoscopic, and/or endosurgical procedures have been developed for making medical treatments, diagnoses, and images of areas along the biliary tract and/or the pancreatic tract. For the purposes of this disclosure, the "biliary tract" and/or the "pancreatic tract" are understood to include various components of the digestive system and include, for example, the various ducts of the biliary tree between the liver and the duodenum as well as the various ducts between the pancreas and the duodenum. Numerous endoscopic and/or endosurgical devices have been developed for making medical treatments, diagnoses, and images of areas along the biliary and pancreatic tracts. Some of these device and/or procedures include biliary catheters, biliary guidewires, biliary stent delivery systems, and the like. In general, these devices are guided to the biliary and/or pancreatic tract by an endoscope (and/or a duodenoscope) that is disposed in the duodenum. Once positioned, various interventions can be performed depending on the needs of the patient and the type of device utilized. Other locations and/or uses are also contemplated for the systems disclosed herein including, for example, urinary tract interventions and/or urological interventions, gynecological interventions, etc.

When delivering a stent such as a drainage stent to the appropriate position within the anatomy, it may be desirable to hold or secure the position of the stent relative to a push catheter, which may be part of the stent delivery system. This allows the clinician to position and deploy the stent accurately at the intended location. One way that the stent may be secured to the push catheter may be with the use of a suture. Conventionally when a suture is utilized to secure a stent to a push catheter, the suture is formed into a loop that is wrapped around the guide catheter (which may extend through the lumen of the push catheter). The suture then extends through one of the barbed openings or flaps formed in the stent and it may be pulled snugly and attached or tied to the end of the push catheter, for example at a hole or opening formed at the distal end of the push catheter. As long as the position of the guide catheter is held stationary relative to the push catheter, this arrangement holds the position of the stent and effectively secures the stent to the push catheter. To release the stent, the guide catheter can be proximally retracted to a point where it exits and is disposed proximally of the loop formed in the suture. When no longer wrapped around the guide catheter, the loop or looped end of the suture is free to simply exit the opening at the barbed flap of the stent such that the stent is released from the push catheter.

While effective, the above-described conventional use of a suture to secure the stent relative to the push catheter is dependent on the manipulation of the guide catheter in order to deploy the stent. Furthermore, should the clinician desire to reposition the stent after deployment (e.g., due to improper or undesirable placement), additional manipulation steps may be required including further manipulation of the guide catheter.

Disclosed herein are a number of delivery systems for delivery a stent (e.g., a drainage stent) to an appropriate position within the anatomy. The delivery systems may use a holding filament or structure such as a suture to secure the position of the stent relative to a push member or catheter. Deployment or release of the stent from the push catheter, however, can be accomplished independently of movement of the guide catheter. Furthermore, the delivery systems disclosed herein may also allow the clinician to "resecure" the sent to the push catheter or otherwise allow for the clinician to reposition the stent, again independently of movement of the guide catheter. Some additional details regarding these and other features of a number of different example stent delivery systems are provided below.

Figure 2:
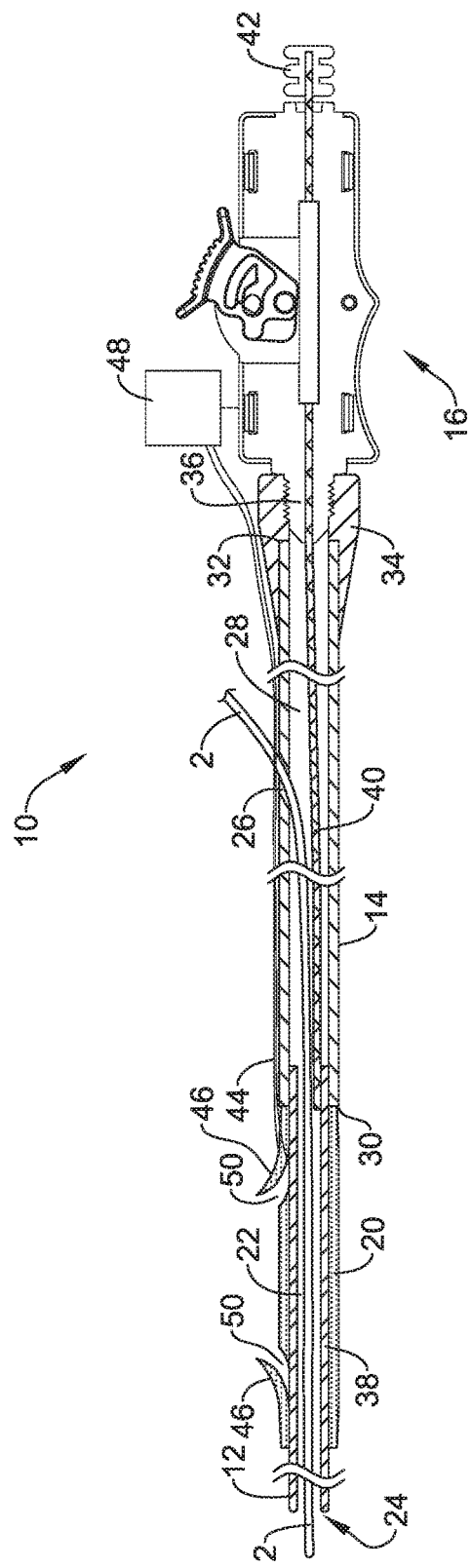
FIG. 2 is a longitudinal cross-sectional view of the stent delivery system illustrated in FIG. 1.

Referring now to FIGS. 1 and 2, there is shown an example medical device, illustrated as a delivery system 10 for delivering, for example, a stent 20 such as a drainage stent to a suitable target location such as, for example, a target along the biliary and/or pancreatic tree. The system 10 may also be used at any other suitable location. The stent 20 may be used to bypass or drain an obstructed lumen, for example along the biliary and/or pancreatic tree, and can be configured for long-term positioning within the body. It should be understood that the terms "drainage stent", "drainage catheter" and "stent" can be used interchangeably with reference to the devices and systems disclosed herein.

The delivery system 10 may be designed for use with a conventional guidewire 2 and may include a guide catheter 12, a push catheter 14, and a handle assembly 16. The guidewire 2 may extend into a lumen 22 of the guide catheter 12, through a distal guidewire port 24, and out a proximal guidewire port 26 formed in a sidewall of the push catheter 14, providing the delivery system 10 with single-operator-exchange (SOE) capabilities. Other embodiments are also contemplated, however, where the delivery system 10 is an over-the-wire (OTW) system.

The guide catheter 12 may be slidably disposed within the lumen 28 of the push catheter 14 and may extend distally from the distal end of the push catheter 14. The stent 20 may be positioned on a distal portion of the guide catheter 12, which may be located distal of the push catheter 14, and the stent 20 may abut the distal end 30 of the push catheter 14. The system 10 may also include a holding filament or suture 44 for releasably connecting the push catheter 14 to the stent 20. Some additional details regarding the holding filament 44 and/or the connection of the stent 20 with the push catheter 14 (and/or other structures of the system 10) are provided below. When the stent 20 has been properly placed, the stent 20 may be disconnected from the push catheter 14 such that the stent 20 remains in the anatomy or body lumen when the push catheter 14 is withdrawn.

The proximal end 32 of the push catheter 14 may be attached to the handle assembly 16. For example, the proximal end 32 may include a female luer lock connector 34 threadably coupled to a threaded male connector 36 of the handle assembly 16. It may be understood, however, that the push catheter 14 may be attached to the handle assembly 16 and extend distally therefrom by other means, such as adhesive bonding, welding, friction fit, interlocking fit, or other suitable means.

The guide catheter 12 may include a distal tubular portion 38 and a proximal elongate wire 40, such as a pull wire, coupled to the distal tubular portion 38. In some instances, the elongate wire 40 may be a wire, filament, thread, portion of a catheter wall, fabric, web, or similar elongate structure. The elongate wire 40 may be coupled to the distal tubular portion 38 at a rotatable connection that may allow rotatable movement between the tubular portion 38 and the elongate wire 40 of the guide catheter 12. The elongate wire 40 may extend through the lumen 28 of the push catheter 14 to the handle assembly 16. In some embodiments, the elongate wire 40 may extend through the handle assembly 16 to a location proximal of the handle assembly 16. The proximal end of elongate wire 40 may terminate at a knob 42 which may be grasped by an operator to manipulate the guide catheter 12.

As shown in FIG. 2, the elongate wire 40 may share the lumen 28 of the push catheter 14 with the guidewire 2 along a portion of the length of the elongate wire 40. Thus, a portion of the elongate wire 40 may extend proximally from the tubular portion 38 along the side of the guidewire 2 through the lumen 28 of the push catheter 14 up to a location where the guidewire 2 exits the proximal guidewire port 26 of the push catheter 14.

As indicated above, the holding filament 44 may secure the stent 20 to the push member. In at least some embodiments, the holding filament 44 is a suture. However, this is not intended to be limiting as the holding filament 44 may take the form of any suitable structure such as a wire, cord, braid, coil, or the like. Indeed, the holding filament 44 may be a mono-filament structure (e.g., made from a singular filament) or multi-filament structure (e.g., made from a plurality of filaments that may or may not be the same). The holding filament may be made from any suitable material including polymers, natural materials, metals, catgut, cotton, and the like, combinations thereof, or any other suitable material including those materials disclosed herein. In some embodiments, more than one holding filaments 44 may be utilized. It should be understood that the terms "holding filament" and "suture" can be used interchangeably with reference to the devices and systems disclosed herein.

The stent 20 may include one or more anchors 46 that are generally disposed near an opening 50 in the stent 20. Anchors 46, for example, may project radially outward from the stent 20 and help to secure or "anchor" the position of the stent 20 within the anatomy when deployed. In at least some embodiments, the anchors 46 are defined by a skived cut in the stent 20 and take the form of a barb or barb-like flap. Other configurations are contemplated.

In at least some embodiments, the suture 44 may wrap around the anchor 46. Such a configuration may also be described as the suture 44 being disposed in the opening 50, at the opening 50, or adjacent the opening 50 of the stent 20. The suture 44, rather than being tied to the push catheter 14, may extend proximally along the push catheter 14 to a position adjacent the handle assembly 16. For example, the suture 44 may extend to a control or actuation member, shown generally at reference number 48. In other embodiments, the ends of the suture 44 may extend back toward the handle assembly 16 and be accessible to the user such that the control 48 is optional or may be omitted. In general, the suture 44 may be free of attachment or securement to the push catheter 14.

The control 48, which may or may not be secured to the handle assembly 16, may allow the clinician to manipulate and/or alter the attachment of the stent 20 to the push catheter 14. For example, the control 48 may allow the user to release one end of the suture 44 (e.g., when the suture is formed as a loop so that two ends extend to the control 48) and pull the other end so that the suture 44 is proximally retracted until the suture 44 is no longer wrapped around the anchor 46. This essentially "frees" the stent 20 from the pusher member 14. If the control 48 is not being utilized, the same thing can be accomplished by the user releasing one of the ends of the suture 44 and proximally retracting the other end until the suture 44 is no longer wrapped around the anchor 46. In other embodiments, the user may actuate the control 48 or otherwise pull on the suture such that sufficient force is generated to sever the suture 44 (e.g., break, cut, or otherwise become dissociated with the anchor 46) and effect release of the stent 20. For example, the suture 44 may be predisposed to break at a predetermined force by altering the suture by thinning (e.g., in diameter) a portion thereof, by omitting structure that might otherwise strengthen or support the suture (e.g., braids, etc.), notching, making the suture 44 brittle (e.g., brittle at a pre-determined location), etc. Other configurations are contemplated for releasing the stent 20 from the pusher member 14.

In addition to being configured to release the stent 20 from the pusher member 14 and/or to deploy the stent 20, the holding filament/suture 44 may also be used to reposition the stent 20. For example, the suture 44 may be partially actuated. For the purposes of this disclosure, partially actuating the suture 44 may be understood to be "loosening" or otherwise be manipulating the suture 44 so as to create enough slack therein that the pusher member 14 can be moved a relatively short distance away from to the stent 20. This may allow the stent 20 to at least partially deploy or be placed within the anatomy. The user may then observe or visualize the position of the stent 20. If the user decides that the position of the stent 20 needs to be altered, the slack in the suture 20 can be removed (e.g., the suture 20 can be "tightened") so that the stent 20 once again become secured to the pusher member 14 and the stent 20 can be repositioned (e.g., urged distally and/or proximally, as desired). Once the user is satisfied with the position of the stent 20, the suture 44 can be "fully actuated" (e.g., in one of the manners disclosed herein or any other suitable manner) so that the stent 20 is deployed and the delivery device 10 can be removed from the anatomy.

Figure 3:
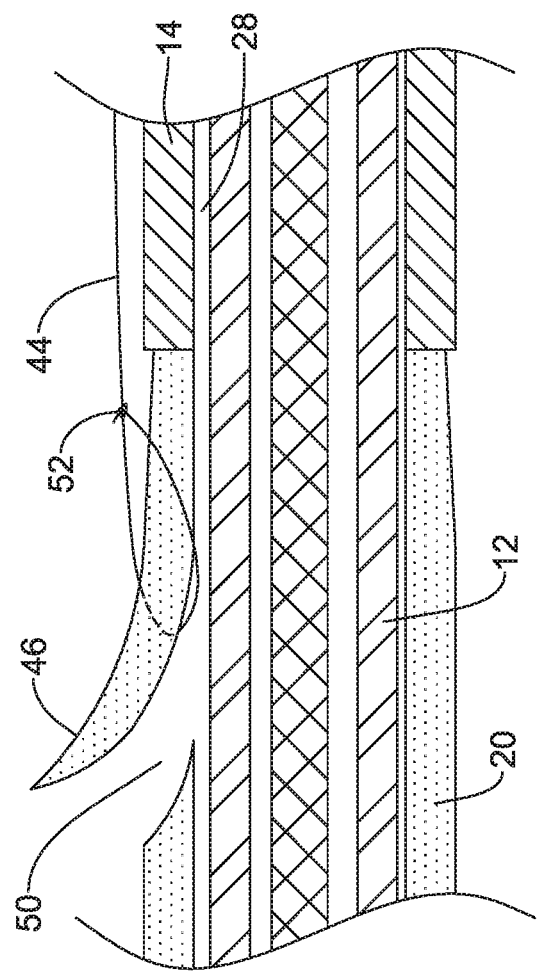
FIG. 3 illustrates an example arrangement for a holding filament that may be utilized with the stent delivery system illustrated in FIGS. 1-2.

FIG. 3 illustrates another example arrangement for the suture 44 that may be utilized with the delivery device 10. In this embodiment, the suture 44 be wrapped around the anchor 46 and be tied into a knot 52. According to this embodiment, only a singular "end" of the suture 44 (rather than two opposite ends) may extend to the control 48 or otherwise be accessible to the user. To release the stent 20, sufficient force may be exerted onto suture 44 so as to sever the suture 44 (e.g., at or adjacent the knot 52) and release the stent 20. Alternatively, the knot 52 may be a slip-type knot so that the knot 52 can be untied by pulling on the end of the suture 44. In still other embodiments, a secondary suture (not shown) may be coupled to the knot 52 and, for example, extend proximally to the handle assembly 16. The secondary suture may be actuated to release the knot 52. Numerous other configurations are contemplated.

Figure 4:
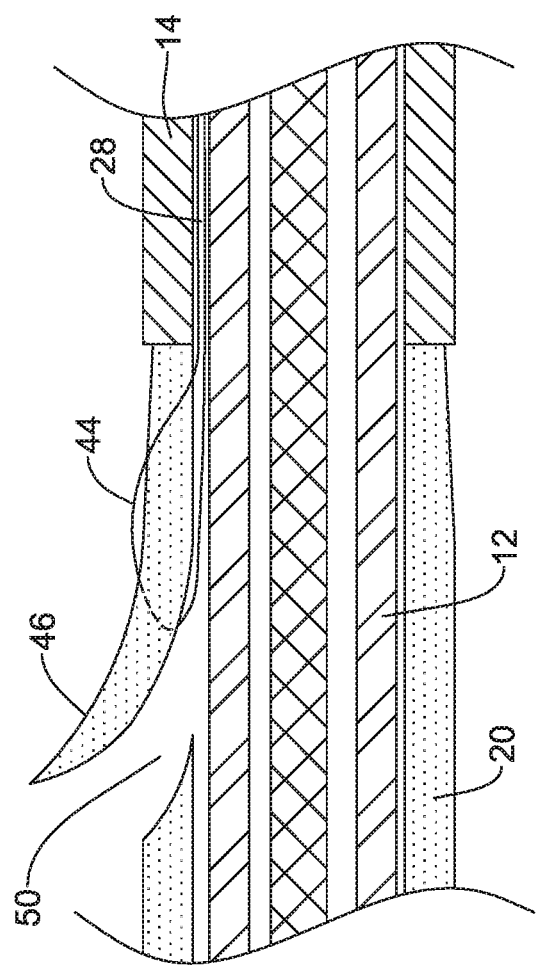
FIG. 4 illustrates another example arrangement for a holding filament that may be utilized with the stent delivery system illustrated in FIGS. 1-2.
Figure 5:
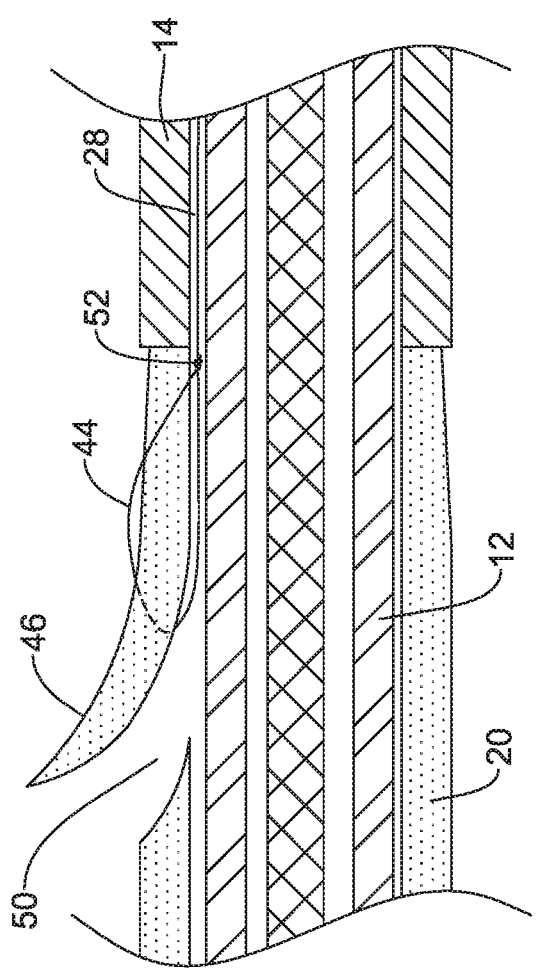
FIG. 5 illustrates another example arrangement for a holding filament that may be utilized with the stent delivery system illustrated in FIGS. 1-2.

FIGS. 4-5 illustrates additional example arrangements for the suture 44 that may be utilized with the delivery device 10. In the embodiment illustrated in FIG. 4, the suture 44 again wraps around the anchor 46. However, instead of being disposed along the exterior of the push catheter 14, for example as shown in FIGS. 1-3, the suture 44 extends along the interior of the push catheter 14, for example through the lumen 28 of the push catheter 14 or otherwise between the push catheter 14 and the guide catheter 12. In the embodiment illustrated in FIG. 5, the suture 44 may extend through the opening 50 in the stent 22 and tied into a knot 52, and the singular end may extend proximally through the lumen 28 of the push catheter 14 or otherwise between the push catheter 14 and the guide catheter 12.

Other embodiments are also contemplated where the suture 44 may extend through the opening 50 of the stent 20. According to these embodiments, one end of the suture 44 may extend along the exterior of the push catheter 14. The other end of the suture 44 may extend along the interior of the push catheter 14 or the other end of the suture 44 may follow the interior of the stent 20, extend between the proximal end of the stent 20 and the distal end 30 of the push catheter 14, and then extend along the exterior of the push catheter 14. Alternatively, one end of the suture 44 may extend along the interior of the push catheter 14 and the other end of the suture 44 may either extend along the interior of the push catheter 14 or it may follow the exterior of the stent 20, extend between the proximal end of the stent 20 and the distal end 30 of the push catheter 14, and then extend along the interior of the push catheter 14.

Figure 6:
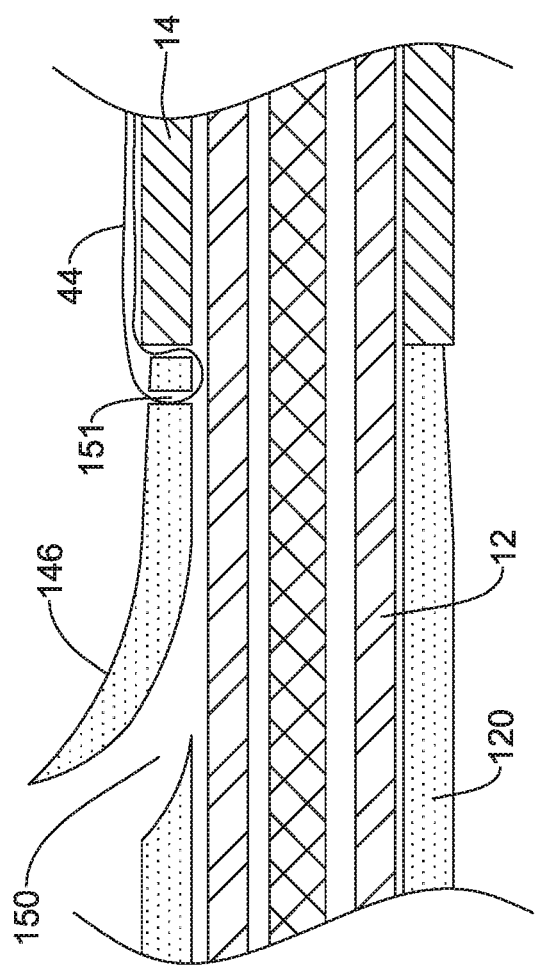
FIG. 6 illustrates another example arrangement for a holding filament that may be utilized with the stent delivery system illustrated in FIGS. 1-2.
Figure 7:
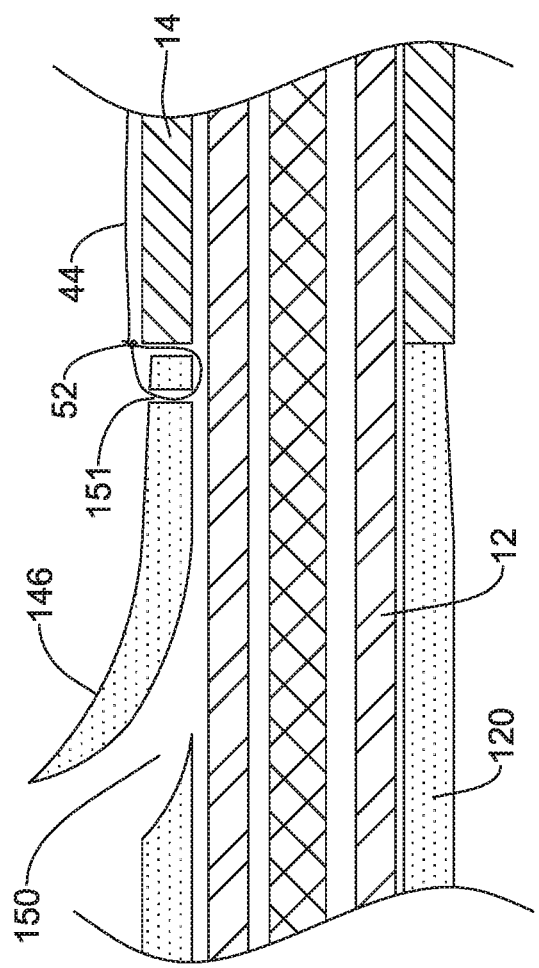
FIG. 7 illustrates another example arrangement for a holding filament that may be utilized with the stent delivery system illustrated in FIGS. 1-2.

FIG. 6-7 illustrate additional example arrangements for the suture 44 that may be utilized with the delivery device 10. In the embodiment illustrated in FIG. 6, the stent 120 has an opening 151 formed therein. The opening 151 is different from the opening 150 formed at the anchor 146. For example, the opening 151 may be positioned adjacent to the anchor 146, proximal of the anchor 146, or at any other suitable location. Indeed, in some embodiment, the stent 120 may not have an opening at the anchor 146. This may be true in this or any other embodiment disclosed herein. The suture 44 may be looped through the opening 151 and then the suture 44 may along the exterior of the push catheter 14, for example, to the control 48. In the embodiment illustrated in FIG. 7, the suture 44 may be looped through the opening 151 and tied into a knot 52. The end of the suture 44 may extend along the exterior of the push catheter 14 to the control 48.

Figure 8:
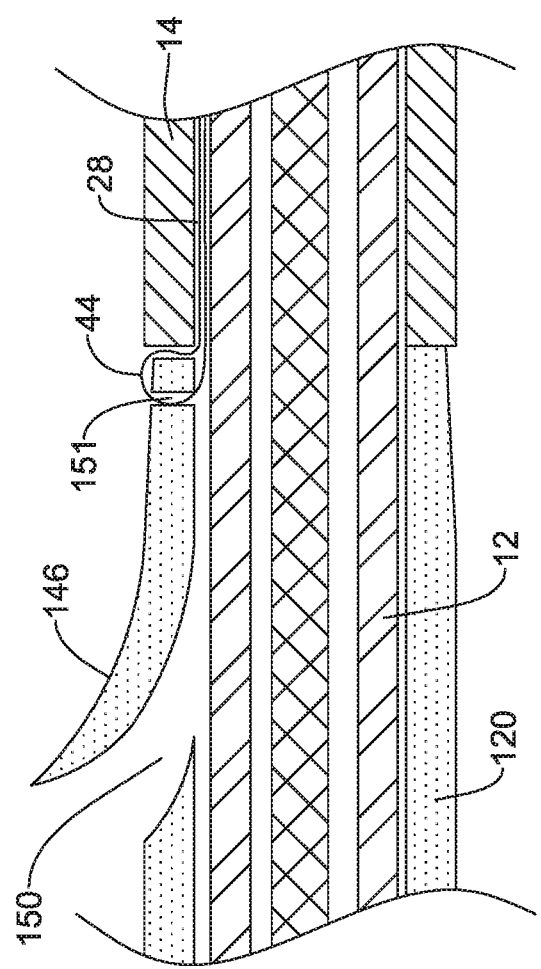
FIG. 8 illustrates another example arrangement for a holding filament that may be utilized with the stent delivery system illustrated in FIGS. 1-2.
Figure 9:
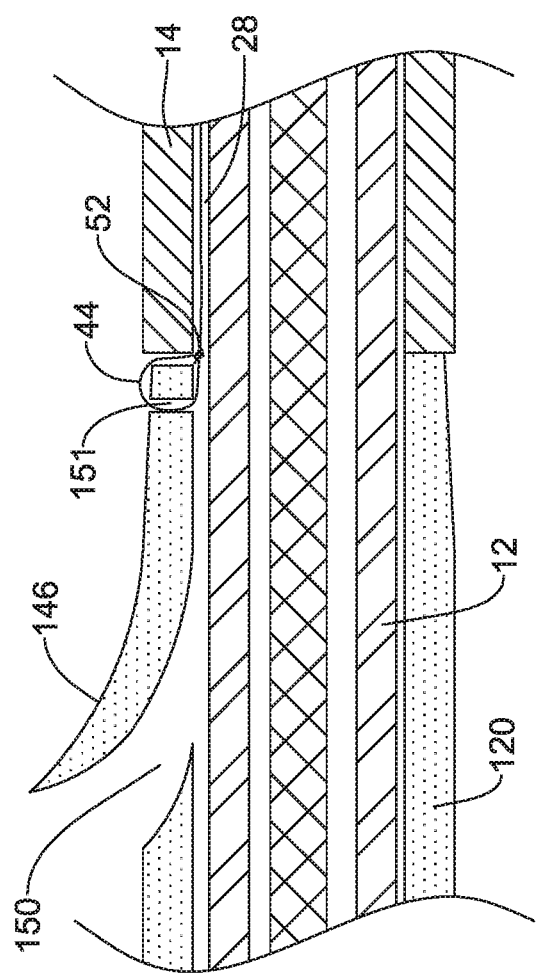
FIG. 9 illustrates another example arrangement for a holding filament that may be utilized with the stent delivery system illustrated in FIGS. 1-2.

FIGS. 8-9 illustrates additional example arrangements for the suture 44 that may be utilized with the delivery device 10. In the embodiment illustrated in FIG. 8, the suture 44 is again looped through the opening 151 in the stent 120 and then extends along the interior of the push catheter 14, for example through the lumen 28 of the push catheter 14 or otherwise between the push catheter 14 and the guide catheter 12. In the embodiment illustrated in FIG. 9, the suture 44 is again looped through the opening 151 in the stent 120 and tied into a knot 52 and the singular end extends along the interior of the push catheter 14, for example through the lumen 28 of the push catheter 14 or otherwise between the push catheter 14 and the guide catheter 12.

Figure 10:
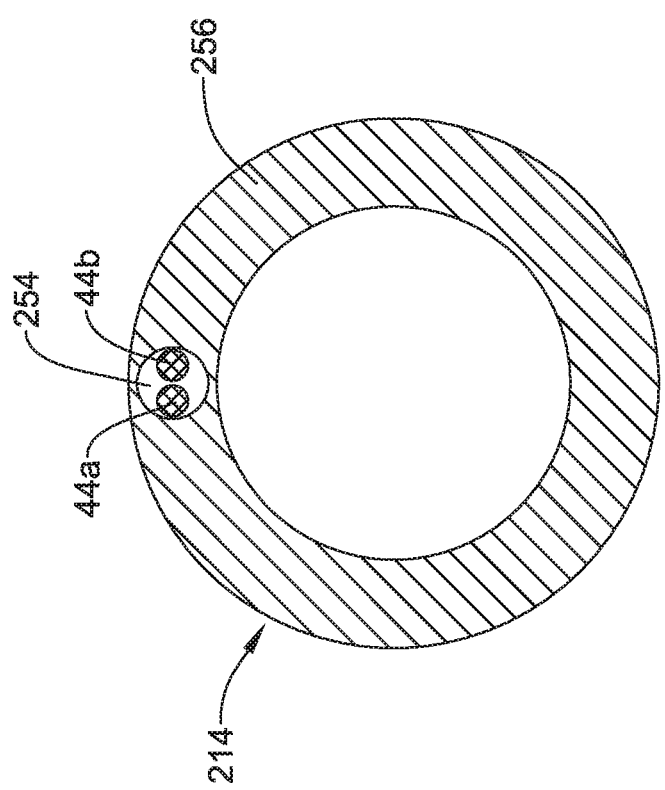
FIG. 10 is a cross-sectional view of an example push catheter that may be utilized with the stent delivery system illustrated in FIGS. 1-2.
Figure 11:
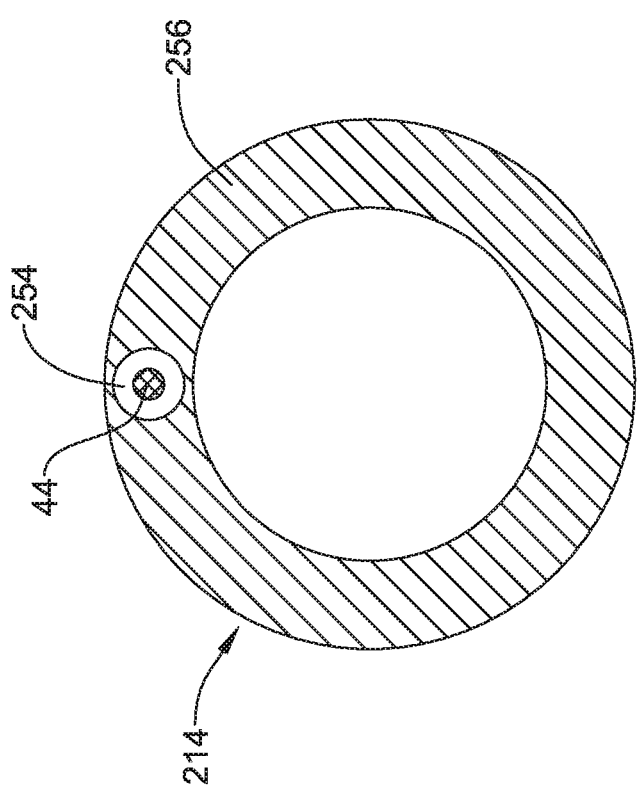
FIG. 11 is a cross-sectional view of another example push catheter that may be utilized with the stent delivery system illustrated in FIGS. 1-2.
Figure 12:
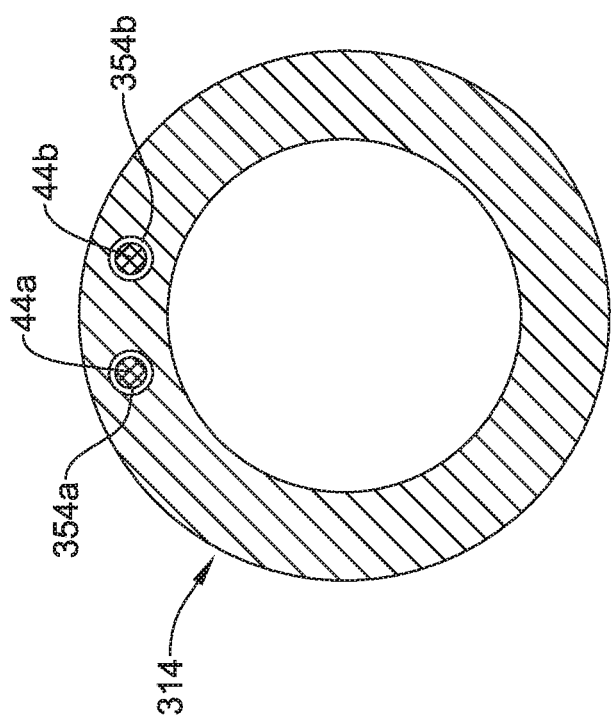
FIG. 12 is a cross-sectional view of another example push catheter that may be utilized with the stent delivery system illustrated in FIGS. 1-2.

FIGS. 10-12 illustrates alternative example push catheters that may be utilized with the delivery system 10. In general, these push catheters have one or more openings or lumens formed in the wall of the push catheter. The suture 44 may pass through the lumen(s) to a position adjacent the handle assembly 16 so that the suture 44 may be associated with the control 48 or otherwise accessible to the user. The use of such push catheters having one or more lumens in the wall may be desirable for a number of reasons. For example, the use of push catheters having one or more lumens in the wall may allow the suture 44 to extend proximally back toward the handle assembly 16 without being either exposed to either the exterior of the push catheter 14 or the interior the push catheter 14 (e.g., between the push catheter 14 and the guide catheter 12) where the suture 44 could get caught on, break, or otherwise disrupt other structures of the delivery system 10 and/or interrupt proper delivery of the stent (e.g., the stent 20/120).

FIG. 10 illustrates the push catheter 214 having a single opening or lumen 254 formed in the wall 256 thereof. In embodiments such as those shown in FIGS. 1-2, 4, 6, and 8, where the two opposite ends of the suture 44 may extend back toward the handle assembly 16, the single lumen 254 allows both ends of the suture 44 (which are shown in FIG. 10 and bear reference numbers 44a/44b) to extend proximally through a singular channel. In embodiments such as those shown in FIGS. 3, 5, 7, and 9, where the suture 44 is tied into a knot 52 and a singular "end" extends back toward the handle assembly 16, the single lumen 254 may allow this singular end of the suture to extend proximally toward the handle assembly as shown in FIG. 11. In the embodiment shown in FIG. 12, a pair of lumens 354a/354b are formed in the wall of the push catheter 314. According to this embodiment, each of the ends 44a/44b of the suture 44 can extend through its own lumen 354a/354b.

Figure 13:
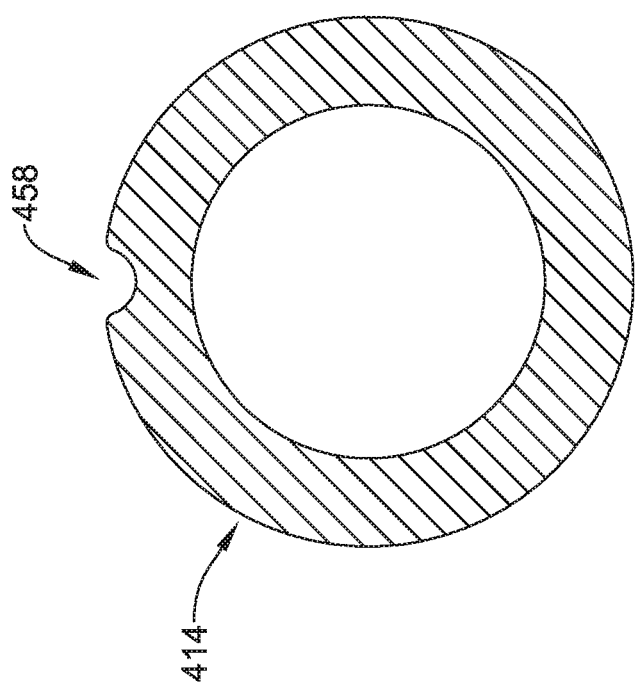
FIG. 13 is a cross-sectional view of a portion of another example push catheter.
Figure 14:
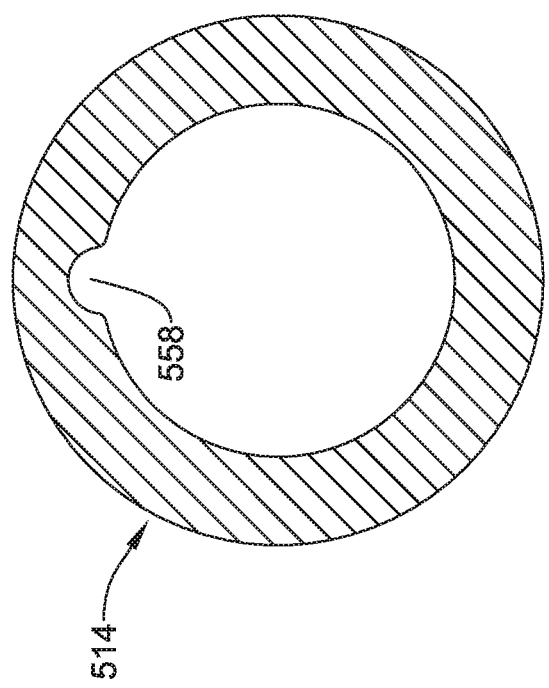
FIG. 14 is a cross-sectional view of a portion of another example push catheter.
Figure 15:
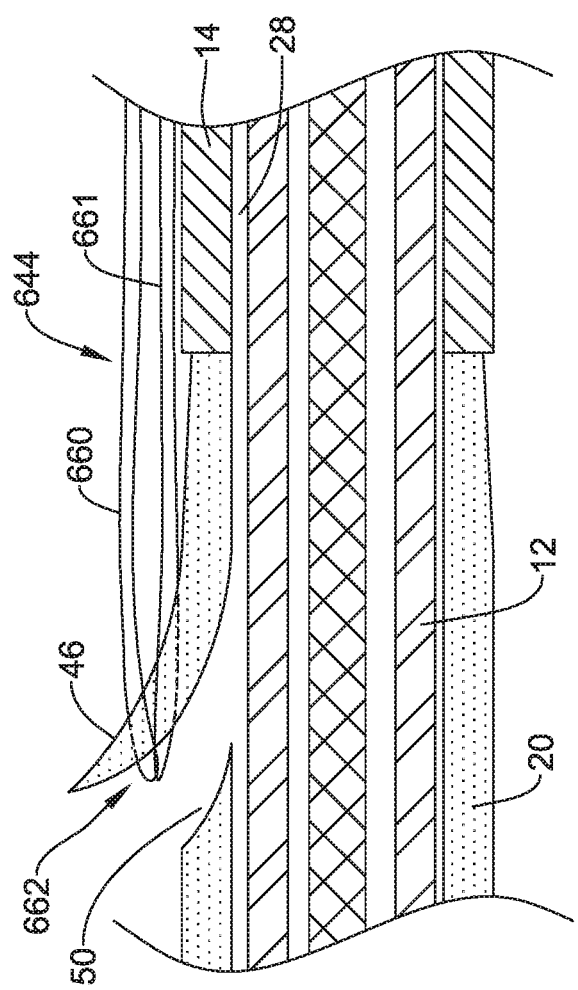
FIG. 15 illustrates another example arrangement for a holding filament that may be utilized with a stent delivery system.
Figure 16:
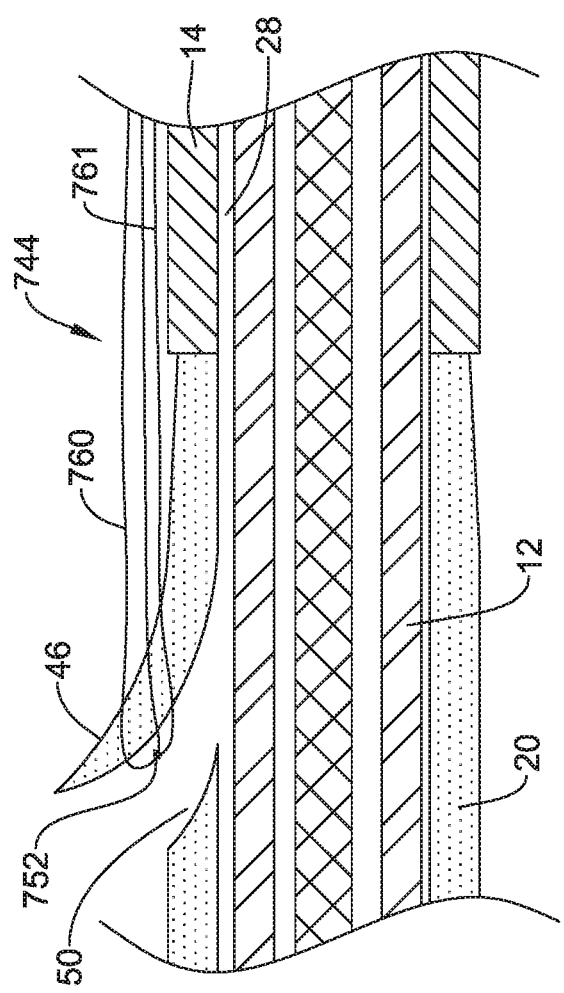
FIG. 16 illustrates another example arrangement for a holding filament that may be utilized with a stent delivery system.

FIGS. 13-14 illustrate additional contemplated push catheters. For example, FIG. 13 illustrates the push catheter 414 having a groove 458. In this embodiment, the groove 458 is formed in the outer surface of the push catheter 414. The groove 458 may act as a guide for the suture or holding filament. The groove 458 may extend along one or more discrete portions of the length of the push catheter 414 or along essentially the full length thereof. Similarly, FIG. 14 illustrates the push catheter 514 with a groove 558 formed along an inner surface. Just like groove 458, groove 558 may extend along one or more discrete portions of the length of the push catheter 514 or along essentially the full length thereof. Either or both of the grooves 458/558 may be utilized in any of the embodiments disclosed herein.

Figure 17:
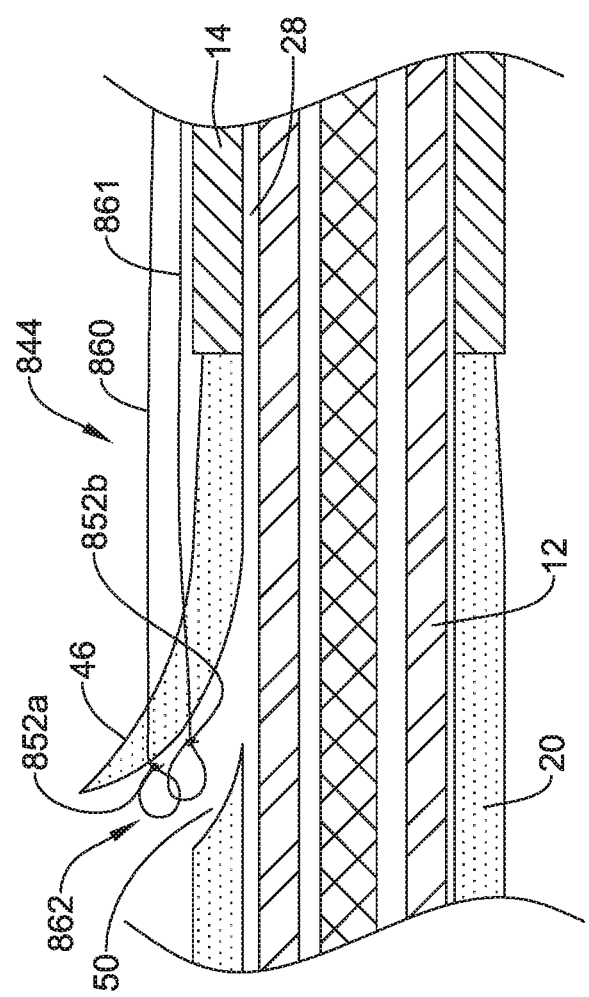
FIG. 17 illustrates another example arrangement for a holding filament that may be utilized with a stent delivery system.

FIGS. 15-19 illustrate additional example arrangements for a holding filament that may be utilized with a stent delivery system including any of those disclosed herein. For example, in FIG. 15 the holding filament 644 includes a first portion 660, which may take the form of a looped wire, and a second portion 661, which may also take the form of a looped wire. The portions 660/661 may loop or otherwise intersect with one another at an intersection 662 and they may extent around the anchor 46. Similarly, in FIG. 16 the holding filament 744 includes a first portion 760 taking the form of a loop and a second portion 761 taking the form of a single filament. The portions 760/761 may be joined at a knot 752 and they may extend around the anchor 46. Finally, as shown in FIG. 17 the holding filament 844 may include a first portion 860 taking the form of a single filament tied with a knot 852a to form a loop and a second portion 861 also taking the form of a single filament tied with a knot 852b to form a loop. The loops may join together at an intersection 862 and the portions 860/861 may extend around the anchor 46. Any of the holding filaments and/or arrangements of holding filaments may be utilized with any of the systems disclosed herein.

Figure 18:
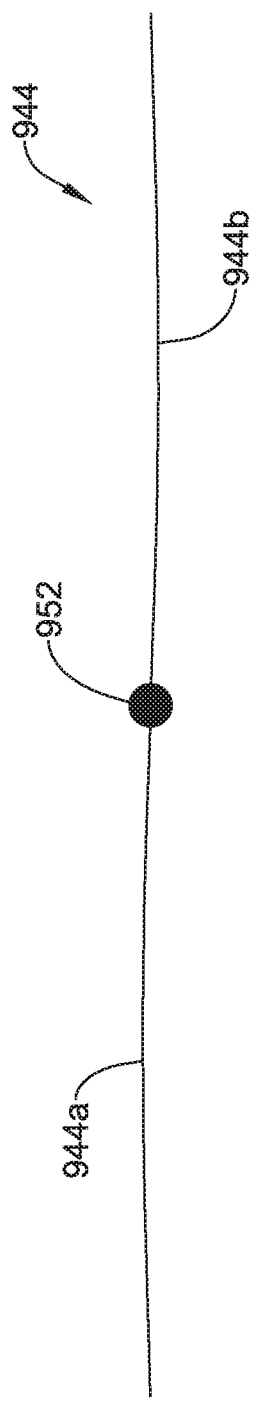
FIG. 18 is a plan view of an example arrangement for a holding filament.

FIGS. 18-19 illustrate additional holding filament arrangements that may also be used with any of the systems disclosed herein. For example, one example holding filament 944, as shown in FIG. 18, may include a first portion 944a and a second portion 944b joined together with a bond 952. In some embodiments, the bond 952 may be an adhesive. Other bonds may also be utilized. Similarly, FIG. 19 illustrates another example holding filament 1044 that includes a first looped portion 1044a and a second looped portion 1044b joined together with a bond 1052. The bond 1052, just like the bond 952, may include adhesive or any other suitable bonding material.

The materials that can be used for the various components of the delivery system 10 may include those commonly associated with medical devices. For simplicity purposes, the following discussion makes reference to the push catheter 14. However, this is not intended to limit the devices and methods described herein, as the discussion may be applied to any of the other structures and/or components of the delivery devices disclosed herein.

The push catheter 14 and/or other components of the delivery device 10 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the push catheter 14 and/or other components of the delivery device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 10 to achieve the same result.

In some embodiments, a degree of Magnetic Resonance Imaging (MRI) compatibility is imparted into the delivery device 10. For example, to enhance compatibility with MRI machines, it may be desirable to make the push catheter 14, or other portions of the delivery device 10, in a manner that would impart a degree of MRI compatibility. For example, the push catheter 14, or portions thereof, may be made of a material that does not substantially distort the image and create substantial artifacts (i.e., gaps in the image). Certain ferromagnetic materials, for example, may not be suitable because they may create artifacts in an MM image. The push catheter 14, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

The push catheter 14 and/or other component the delivery system 10 may be made from or otherwise include a polymer or polymeric material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

In some embodiments, the exterior surface of the delivery device 10 may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the delivery device 10. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

The arrangement of the various structures of the delivery system 10 may vary. In some embodiments, the system 10 may include any of the structures or utilize any of the arrangements of structures that are disclosed in U.S. Pat. Nos. 5,152,749; 5,334,185; 5,921,952; 6,248,100; 6,264,624; and 6,562,024, the entire disclosures of which are herein incorporated by reference.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A stent delivery system, comprising:
   a guide member having a proximal portion and a distal portion;
   a stent disposed about the distal portion of the guide member, wherein the stent has a wall having an opening formed therein;
   a pusher member having a proximal end and a distal end;
   wherein the pusher member is disposed about the guide member such that the distal end of the pusher member abuts a proximal end of the stent;
   a holding filament disposed adjacent the opening and extending to the proximal portion of the guide member, wherein the holding filament includes a first filament portion, a second filament portion and a loop portion extending between the first filament portion and the second filament portion, wherein the loop portion of the holding filament is configured to releasably secure the position of the stent relative to the pusher member, and wherein the holding filament can be released from the stent independently of movement of the guide member;

wherein an exterior surface of the pusher member includes a groove extending along at least a portion of a longitudinal axis thereof; and wherein the first and second filament portions extend along the groove.

2. The stent delivery system of claim 1, wherein the stent is configured to be in either a first configuration or a second configuration where the stent is releasably secured relative to the pusher member with the holding filament and a second configuration where the holding filament is released from the stent.

3. The stent delivery system of claim 2, wherein the guide member extends through the stent in both the first and second configurations.

4. The stent delivery system of claim 1, wherein the holding filament is actuatable from a control disposed at the proximal portion of the guide member.

5. The stent delivery system of claim 1, wherein the holding filament includes a knot that can be untied when the holding filament is pulled.

6. The stent delivery system of claim 1, wherein the holding filament includes a first portion and a second portion joined together with an adhesive bond.

7. The stent delivery system of claim 1, wherein the holding filament is predisposed to break.

8. The stent delivery system of claim 1, wherein the stent includes an anchor.

9. The stent delivery system of claim 8, wherein the holding filament is wrapped around the anchor.

10. The stent delivery system of claim 8, wherein the opening formed in the stent is positioned adjacent to the anchor and the suture extends through the opening.

11. A stent delivery system, comprising:
a guide member having a proximal portion and a distal portion;
a stent disposed about the distal portion of the guide member, wherein the stent has a wall having an opening formed therein;
a pusher member disposed about the guide member and positioned proximal of the stent; and
a holding filament disposed adjacent the opening and extending to the proximal portion of the guide member, wherein the holding filament includes a first filament portion, a second filament portion and a loop portion extending between the first filament portion and the second filament portion, wherein the loop portion is configured to releasably secure the position of the stent relative to the pusher member, and wherein the holding filament can be released from the stent independently of movement of the guide member;
wherein the pusher member has a tube wall having a proximal end and a distal end;
wherein the pusher member has a pair of lumens defined in the tube wall that extend along a longitudinal axis between the proximal end and the distal end; and
wherein at least a portion of the first filament portion extends through one of the lumens and at least a portion of the second filament portion extends through another of the lumens.

12. The stent delivery system of claim 11, wherein the stent is configured to be in either a first configuration where the stent is releasably secured relative to the pusher member with the holding filament and a second configuration where the holding filament is released from the stent.

13. The stent delivery system of claim 12, wherein the guide member extends through the stent in both the first and second configurations.

14. The stent delivery system of claim 11, wherein the holding filament is actuatable from a control disposed at the proximal portion of the guide member.

15. The stent delivery system of claim 11, wherein the holding filament includes a knot that can be untied when the holding filament is pulled.

16. The stent delivery system of claim 11, wherein first and second filament portions are joined together with an adhesive bond.

17. The stent delivery system of claim 11, wherein the holding filament is predisposed to break.

18. The stent delivery system of claim 11, wherein the stent includes an anchor and wherein the holding filament is wrapped around the anchor.

19. The stent delivery system of claim 11, wherein the stent includes an anchor, wherein the opening formed in the stent is positioned proximal to the anchor, and wherein the suture extends through the opening.

20. A stent delivery system, comprising:
a guide member having a proximal portion and a distal portion;
a stent disposed about the distal portion of the guide member, wherein the stent has a wall having an opening formed therein;
a pusher member having a proximal end, a distal end and a lumen extending therebetween;
wherein the pusher member is disposed about the guide member such that the distal end of the pusher member abuts a proximal end of the stent;
a holding filament disposed adjacent the opening and extending to the proximal portion of the guide member, wherein the holding filament includes a first filament portion, a second filament portion and a loop portion extending between the first filament portion and the second filament portion, wherein the loop portion of the holding filament is configured to releasably secure the position of the stent relative to the pusher member;
wherein an interior surface of the pusher member lumen includes a groove extending along a longitudinal axis thereof; and
wherein the first and second filament portions extend along the groove.

* * * * *